United States Patent [19]

Bruckner et al.

[11] Patent Number: 4,851,449

[45] Date of Patent: Jul. 25, 1989

[54] ODORLESS AROMATIC DIALDEHYDE DISINFECTING AND STERILIZING COMPOSITION

[75] Inventors: Norman I. Bruckner, Plano; Michael D. Gordon; Ronald G. Howell, both of Arlington, all of Tex.

[73] Assignee: Surgikos, Inc., Arlington, Tex.

[21] Appl. No.: 53,208

[22] Filed: May 21, 1987

[51] Int. Cl.$^4$ .............................................. A61K 31/11
[52] U.S. Cl. ...................................... 514/698; 514/699
[58] Field of Search ............... 514/699, 694, 695, 705, 514/698

[56] References Cited

U.S. PATENT DOCUMENTS

| | | | |
|---|---|---|---|
| 3,016,328 | 1/1962 | Pepper et al. | 167/22 |
| 3,282,775 | 11/1966 | Stonehill | 167/22 |
| 3,708,263 | 1/1973 | Boucher | 21/54 A |
| 3,912,450 | 10/1975 | Boucher | 21/54 A |
| 3,968,248 | 7/1976 | Boucher | 424/333 |
| 3,968,250 | 7/1976 | Boucher | 424/333 |
| 3,983,252 | 9/1976 | Buchalter | 424/333 |
| 4,048,336 | 9/1979 | Winicov et al. | 535/445 |
| 4,436,754 | 3/1984 | Jacobs | 514/694 |

OTHER PUBLICATIONS

Rein et al., Zentralblatt fuer Bakteralogie, Parasitenkunde, Infektionskrankheitec und Hygiene, 1 Abt. Orig. B 172, pp. 508–519 (1981), cited at pp. 1 and 2 of the specification.

Rehn & Nolte, Zentralblatt fuer Bakteralogie, Parasitenkunde, Infektionskrankheitec und Hygiene, 1 Abt. Orig. B168, pp. 507–516 (1979).

Primary Examiner—Douglas W. Robinson
Assistant Examiner—R. Kearse
Attorney, Agent, or Firm—Michael Q. Tatlow; Charles J. Metz

[57] ABSTRACT

An odorless sterilizing and disinfecting solution containing 0.025 to 1.0 weight percent phthalaldehyde.

5 Claims, No Drawings

ODORLESS AROMATIC DIALDEHYDE DISINFECTING AND STERILIZING COMPOSITION

FIELD OF INVENTION

This invention relates to stable, odorless sterilizing and high level disinfecting compositions which contain a water soluble aromatic dialdehyde as the active ingredient. The aromatic dialdehyde employed is 1,2-benzenedicarboxaldehyde, commonly referred to as phthalaldehyde.

PRIOR ART

Saturated dialdehyde sterilizing and disinfecting compositions are well known. Pepper et al., U.S. Pat. No. 3,016,328; Stonehill, U.S. Pat. No. 3,282,775; Boucher, U.S. Pat. Nos. 3,708,263, 3,912,450, 3,968,248 and 3,968,250; and Buchalter, U.S. Pat. No. 3,983,252 all disclose the use of glutaraldehyde in aqueous or alcoholic solutions used to disinfect or sterilize medical devices or environmental surfaces.

Jacobs, U.S. Pat. No. 4,436,754 discloses low odor glutaraldehyde sterilizing and disinfection compositions.

Rehn and Nolte in *Zentralblatt fuer Bakteralogie, Parasitenkunde, Infektionskrankheitec und Hygiene.*, 1 Abt. Orig. B 168, pp. 507-516 (1979) disclose that a range of aromatic monoaldehydes and one aromatic dialdehyde, terephthalaldehyde, have bacteriostatic and fungistatic activity.

Rehn, Nolte, and Zerling in *Zentralblatt fuer Bakteralogie, Parasitenkunde, Infektionskrankheitec und Hygiene,* 1 Abt. Orig. B 172, pp 508-519 (1981) disclose that phthalaldehyde, isophthalaldehyde and terephthalaldehyde all have bacteriostatic and fungistatic activity.

Commercially available high level disinfecting glutaraldehyde compositions of the type disclosed in the above mentioned U.S. Patents have long been considered to be effective against a broad range of microorganisms, including *Mycobacterium tuberculosis* in ten (10) minutes at a temperature of 20° C. The test employed to make the determination of effectiveness was the AOAC Tuberculocidal Test, as specified in *Official Methods of Analysis* of the Association of Official Analytical Chemists, 14th Edition, 1984, Sections 4,045-4.050. In this Test, the organism employed is *Mycobacterium bovis* BCG.

It is now apparent that the standard AOAC test method gives highly erratic and variable results. This test method can show that a disinfectant composition is effective against *Mycobacterium bovis* BCG in 10 minutes, when in fact it is much less effective than the test indicated. An improved test method, which is both reproducible and quantitative, has been developed. The new test method uses the same test organism as the above mentioned AOAC Tuberculocidal Test. In this new test method, nine milliliters (ml) of the germicide to be tested is placed in a tube, put into a water bath and allowed to come to the desired temperature. One ml of the test organism (*M. bovis* BCG) is added to the tube containing the germicide to be tested. At appropriate time intervals, aliquots of the germicide-cell suspension are removed and added directly to an equal volume of appropriate neutralizer and mixed thoroughly. Ten-fold dilutions of the neutralized sample are prepared with saline dilution blanks. One ml of the appropriate dilutions are collected on the surface of membrane filters having a pore size of 0.45 micrometers. The filters are then washed with at least 50 ml of saline. The filters are placed on agar plate and incubated in plastic bags for 15 to 20 days at 37° C. The surviving colonies are then counted. Survival curves are constructed to determine the tuberculocidal activity of the solution. The data is plotted as $S/S_o$ vs. time. $S_o$ is the initial viable count of the test organism culture and S is the viable count at each time point.

When commercial glutaraldehyde solutions are tested using the new quantitative test method, these compositions do not kill the required $1 \times 10^5$ *Mycobacterium bovis* BCG in 10 minutes at 20° C. The additional exposure time required for complete kill at 20° may be as much as several hours. This exposure time becomes impractical, since the desired turn-around time for disinfection of equipment, especially heat-sensitive fiberoptic endoscopes, in the hospital is 30 minutes or less. In order to achieve this equipment turn-around time, a disinfection time of 10 minutes or less is required. In order to obtain a 10 minute kill time, a temperature of 30° C. is required. Since the normal hospital room temperatures are between 20° C. and 25° C., additional costs associated with heating conventional glutaraldehyde compositions would be required to kill all the organisms within the desired 10 minute time frame.

High level disinfectants are not only capable of rapid kill against Mycobacteria, but are effective against the resistant nonlipid and small viruses and with extended exposure times, capable of actual sterilization. It is well known by one skilled in the art that the degree of effectiveness of high level disinfectants is not only controlled by temperature and contact time, but is dependent on active ingredient content and the solution pH. The previously cited references about aromatic dialdehydes do not recognize that phthalaldehyde is a high level disinfectant. It has excellent activity against *Mycobacterium tuberculosis* and Poliovirus Type I. These references also do not recognize that the corresponding 1,3- and 1,4-isomers have little if any high level disinfecting activity. Compositions which contain low concentrations of phthalaldehyde (e.g., 0.25%) as the sole active ingredient are effective against the above-mentioned organisms in 10 minutes or less at a temperature of 20° C. Phthalaldehyde, at the same low concentrations, has sporicidal activity against *Bacillus subtilis* and *Clostridium sporogenes* spores in 24 hours at a temperature of 20° C. At higher concentrations (e.g., 1.0%) of phthalaldehyde, sterilization is achieved in 10 hours. The sporicidal and high level disinfecting activities of compositions with phthalaldehyde are maintained over the pH range 3 to 9.

Storage stability and ease of product use are two important considerations when selecting sterilizing and high level disinfecting solutions. Glutaraldehyde-based compositions are more effective as high level disinfecting and sterilizing solutions at alkaline pH than at neutral or acidic pH values. However, glutaraldehyde and other similar aldehydes with alpha hydrogens autopolymerize at an alkaline pH. Compositions containing these aldehydes at an alkaline pH experience a reduction in the effective concentration of the aldehyde with time and, therefore, have limited storage stability. In order to overcome this problem, the aldehyde composition must be packaged in two or more components. These aldehydes can be formulated in an aqueous solution at an acid pH, and activated with an alkalinating agent immediately prior to use, shifting the pH to the alkaline range. This procedure is disclosed in the prviously-mentioned Pepper et al. patent, U.S. Pat. No. 3,016,328. Unlike the aforementioned aldehydes, phthalaldehyde does not have alpha hydrogens and therefore cannot undergo autopolymerization at an alkaline pH. Compositions containing phthalaldehyde can be formulated as a single component. These compositions have excellent stability over a pH range of 3 to 9. They do not lose their effectiveness during storage.

Glutaraldehyde, at normal use concentrations, has been reported by some hospital personnel to have a pungent odor and be irritating to the eyes and nasal passages. Jacobs, U.S. Pat. No. 4,436,754, discloses the use of glycol additives to reduce the odor and irritation properties of glutaraldehyde compositions. Compositions containing phthalaldehyde as the sole active ingredient are odorless and nonirritating to the eyes and nasal passages.

Since equipment turn-around time is very important when considering methods for high level disinfection and sterilization, compositions that do not coagulate blood or fix tissue to equipment are very desirable. In addition, these properties also aid in the disinfection and sterilization process by insuring better surface contact between equipment and the compositions. Glutaraldehydebased compositions tend to coagulate blood and fix tissue to surfaces. Therefore, careful equipment cleaning is a necessary procedure prior to disinfection and sterilization. Phthalaldehyde compositions do not coagulate blood or fix tissue to surfaces. Because of the aforementioned properties and improved efficacy of phthalaldehyde compositions, disinfection and sterilization procedures with these compositions should be faster and more thorough.

SUMMARY OF THE INVENTION

It has now been discovered that compositions containing low levels of the active ingredient phthalaldehyde are high level disinfecting and sterilizing solutions at 20° C. These compositions at pH 3 to 9 are highly effective against not only gram positive/gram negative bacteria and fungi, but also the difficult to kill organisms such as *Mycobacterium tuberculosis*, Poliovirus Type I, and Bacillus subtilis and *Clostridium sporogenes* spores. In addition, phthalaldehyde compositions are odorless and are nonirritating to eyes and mucous membranes. The compositions are stable over a broad pH range and therefore can be packaged as a single component without loss of effectiveness during storage. Phthalaldehyde compositions also do not coagulate blood or fix tissue on equipment surfaces.

DESCRIPTION OF THE INVENTION

Phthalaldehyde has the structure:

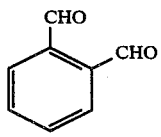

Phthalaldehyde is present in the composition, at use concentration, in amounts of between 0.025% and 1.0% by weight. Higher concentrations, e.g., up to 2%, could be used if desired. The preferred concentration of phthalaldehyde at use dilution is 0.05% to 0.5% by weight. Higher concentrations of phthalaldehyde may be used for shipping the composition to the point of use and the composition could then be diluted with water to the desired use concentration. The limit on the amount of phthalaldehyde used in the concentrate composition is a function of the solubility of phthalaldehyde in water, which is 5% w/w. To achieve compositions of phthalaldehyde with greater than 5% w/w, a water miscible co-solvent can be used. Suitable co-solvents include methanol, ethanol, isopropanol, glycols, tetrahydrofuran, dimethylsulfoxide and dioxane.

An alkalinating or acidifying salt is used in the composition as a buffer to maintain a desired composition pH during storage and use. The buffer may be of the type disclosed in the Pepper et al. U.S. Pat. No. 3,016,328 which is an alkali metal carbonate or bicarbonate, e.g., sodium bicarbonate or potassium bicarbonate or may be a phosphate. The buffer may also be an organic carboxylate such as sodium citrate, sodium acetate, potassium hydrogen phthalate, potassium citrate or potassium acetate. The particular salt or mixture of salts are present in a sufficient amount, 0.05% to 2.5% based on the total weight of the solution, to give the desired pH. The disinfecting properties of the composition are not pH dependent. However, at low phthalaldehyde concentrations (e.g., 0.5% or less) the sporicidal activity of the composition is somewhat pH dependent. The optimal pH range for sporicidal activity is between 6 and 8.

The composition may contain other ingredients such as a surfactant, a corrosion inhibitor, antioxidant, a sequesterent, a dye or a fragrance. The use of these other ingredients is well-known in the art.

The compositions of the present invention may be formulated in one or more components. However, if the composition is formulated in two or more parts, the components are combined immediately prior to use.

In the following Examples, all percentages are weight percentages, based on the total weight of the solutions unless otherwise indicated. In examples showing tuberculocidal test data, the new tuberculocidal test methodology previously described was used.

EXAMPLE I

In this example, a small amount of phthalaldehyde, and amounts of isophthalaldehyde and terephthalaldehyde at their water solubility limit were tested in aqueous solutions to determine their effectiveness against *Mycobacterium bovis* at 20 C. Use of 20% alcohol co-solvent did not significantly increase the amounts of isophthalaldehyde and terephthalaldehyde in the test solution. The solutions were buffered to pH 8.0 with dipotassium hydrogen phosphate. The results are shown in Table I.

TABLE I

| Aromatic Dialdehyde | % Aromatic Dialdehyde (w/w) | Number of Organisms Surviving | | |
|---|---|---|---|---|
| | | 0 min | 10 min | 20 min |
| Phthalaldehyde | 0.10 | $2.4 \times 10^5$ | 0 | 0 |
| Isophthalaldehyde | 0.25 | $2.8 \times 10^5$ | $2.3 \times 10^5$ | $2.3 \times 10^5$ |
| Terephthalaldehyde | 0.10 | $2.8 \times 10^5$ | $3.3 \times 10^5$ | $4.0 \times 10^5$ |

The results show that phthalaldehyde, has excellent tuberculocidal activity at low concentration, while isophthalaldehyde and terephthalaldehyde do not have any appreciable tuberculocidal activity.

EXAMPLE II

A series of solutions containing from 0.01 to 0.75% phthalaldehyde, buffered at pH 8 as in Example I, were tested for their effectiveness in killing Mycobacterium bovis BCG at 20° C. The results are shown in Table II.

TABLE II

| % Phthal- aldehyde (w/w) | Number of Organisms Surviving | | | |
|---|---|---|---|---|
| | 0 min | 2 min | 5 min | 10 min |
| 0.075 | $1.9 \times 10^5$ | $1.2 \times 10^3$ | 0 | 0 |
| 0.05 | $1.9 \times 10^5$ | $5.0 \times 10^3$ | 0 | 0 |
| 0.025 | $1.9 \times 10^5$ | $2.4 \times 10^4$ | $3.2 \times 10^3$ | 0 |
| 0.01 | $1.9 \times 10^5$ | $8.0 \times 10^4$ | $4.0 \times 10^4$ | $2.0 \times 10^4$ |

The results indicate that a concentration of only 0.025% phthalaldehyde is tuberculocidal within 10 minutes at 20° C.

EXAMPLE III

Portions of a solution containing 0.1% phthalaldehyde and dipotassium hydrogen phosphate were adjusted to different pH levels with $H_3PO_4$ and KOH. The solutions were tested against *Mycobacterium bovis* BCG at 20° C. to determine the effect of pH on the effectiveness of the solutions. The results are shown in Table III.

TABLE III

| pH | Number of Organisms Surviving | | |
|---|---|---|---|
| | 0 min | 2 min | 5 min |
| 3 | $3.8 \times 10^5$ | $1.4 \times 10^3$ | 0 |
| 5 | $3.8 \times 10^5$ | $5.2 \times 10^2$ | 0 |
| 7 | $3.8 \times 10^5$ | $2.0 \times 10^1$ | 0 |
| 9 | $3.8 \times 10^5$ | $2.0 \times 10^2$ | 0 |

The results indicate that the tuberculocidal activity of phthalaldehyde is not pH dependent.

EXAMPLE IV

Solutions containing 0.1, 0.5 and 1.0% phthalaldehyde buffered to pH 8 with dipotassium hydrogen phosphate were tested to determine the minimum effective concentration required to inactivate a suspension of about $1 \times 10^6$ (6 logs) Poliovirus Type I after 5 minutes exposure to the solutions at 20° C. The results are shown in Table IV.

TABLE IV

| % Phthalaldehyde (w/w) | Reduction in Virus Titer ($\log_{10}$) |
|---|---|
| 0.1 | 3.0 |
| 0.5 | 5.5* |
| 1.0 | 5.5* |

*Total inactivation of virus

The results show that the minimum effective concentration of phthalaldehyde required to totally inactivate Poliovirus Type I in 5 minutes at 20° C. is between 0.1 and 0.5%.

EXAMPLE V

Solutions containing 0.1% phthalaldehyde buffered to pH 7.5 with dipotassium hydrogen phosphate and pH 6 with potassium acid phthalate were tested against a suspension of about $4.7 \times 10^6$ (6.67 logs) Poliovirus Type I to determine the effect of pH on the reduction of virus titer after 5 minutes exposure to the solutions at 20° C. The results are shown in Table V.

TABLE V

| pH | Reduction in Virus Titer ($\log_{10}$) |
|---|---|
| 6 | 4.2 |
| 7.5 | 4.7 |

The results indicate that the activity of phthalaldehyde against Poliovirus Type I is not significantly dependent on pH over the range of slightly acidic to slightly alkaline.

EXAMPLE VI

A solution containing 0.1% phthalaldehyde buffered to pH 8 with dipotassium hydrogen phosphate was tested to determine its effectiveness in killing *Pseudomonas aeruginosa* (gram -) and Staphylococcus aureus (gram+) at 20° C. using the standard AOAC Use-Dilution Method (AOAC Official Methods of Analysis, 14th edition, 1984, page 67). The results are shown in Table VI.

TABLE VI

| Organism | No. of Positives(Failure)/No. of Total Tests | |
|---|---|---|
| | 5 Min | 10 Min |
| Pseudomonas aeruginosa | 0/30 | 0/30 |
| Staphylococcus aureus | 1/30 | 0/30 |

The results show that phthalaldehyde is cidal against both gram negative and gram positive bacteria within 10 minutes contact time at 20° C.

EXAMPLE VII

The solution tested in Example VI was tested to determine its effectiveness in killing *Trichophyton mentagrophytes* at 20° C. using the standard AOAC Fungicidal Method (AOAC Official Methods of Analysis, 14th edition, 1984, page 69). The results are shown in Table VII.

TABLE VII

| Test Solution | Growth (+) or No Growth (−) | | |
|---|---|---|---|
| | 5 Min | 10 Min | 15 Min |
| Phthalaldehyde (0.1%) | − | − | − |

The results show that phthalaldehyde is fungicidal in 5 minutes at 20° C.

EXAMPLE VIII

Solutions containing from 0.5% to 2.7% phthalaldehyde were tested to determine the minimum effective concentration required to kill spores of *Bacillus subtilis* and Clostridium sporogenes at 20° C. in 10 hours over the pH range 4 to 8 using the standard AOAC Method (AOAC Official Methods of Analysis, 14th edition, 1984, page 72). Solutions at pH 8 were buffered as in Example I and solutions at pH 6 and 4 were buffered with potassium acid phthalate. The results are shown in Table VIII.

TABLE VIII

| % Phthal-aldehyde (w/w) | pH | Total No. of Positives(Failures)/Total No. of Tests | | | |
|---|---|---|---|---|---|
| | | B. subtilis | | C. sporogenes | |
| | | sutures | penicylinders | sutures | penicylinders |
| 2.7 | 8 | 0/30 | 0/30 | 0/30 | 0/30 |
| 1.0 | 8 | 0/30 | 0/30 | 1/30 | 0/30 |
| 0.5 | 8 | 16/30 | 0/30 | 0/30 | 2/30 |
| 1.0 | 6 | 0/30 | 0/30 | 0/30 | 0/30 |
| 0.5 | 6 | 30/30 | 19/30 | 1/30 | 0/30 |
| 1.5 | 4 | 0/30 | 0/30 | 0/30 | 0/30 |
| 1.0 | 4 | 2/30 | 4/30 | 0/30 | 0/30 |

The results indicate that the minimum effective concentration of phthalaldehyde which is sporicidal at 20° C. in 10 hours is about 1% at pH 8, 6 and 4.

EXAMPLE IX

A series of solutions containing from 0.1 to 1.0% phthalaldehyde was tested to determine the minimum effective concentration required to kill spores of B. subtilis and C. sporogenes at 20° C. in 24 hours over the pH range 4 to 8. The results are shown in Table IX. Note: C. sporogenes was note tested in all cases, since B. subtilis was shown to be the more resistant organism in Example VIII.

TABLE IX

| % Phthal-aldehyde (w/w) | pH | Total No. of Positives(Failures)/Total No. of Tests | | | |
|---|---|---|---|---|---|
| | | B. subtilis | | C. sporogenes | |
| | | sutures | penicylinders | sutures | penicylinders |
| 1.0 | 8 | 0/30 | 0/30 | 0/30 | 0/30 |
| 0.5 | 8 | 0/30 | 0/30 | 0/30 | 0/30 |
| 0.25 | 8 | 0/30 | 0/30 | — | — |
| 0.1 | 8 | 14/30 | 11/30 | — | — |
| 1.0 | 6 | 0/30 | 0/30 | 0/30 | 0/30 |
| 0.5 | 6 | 0/30 | 0/30 | 0/30 | 0/30 |
| 0.25 | 6 | 1/30 | 0/30 | — | — |
| 0.1 | 6 | 30/30 | 30/30 | — | — |
| 1.0 | 4 | 0/30 | 0/30 | 0/30 | 0/30 |
| 0.5 | 4 | 7/30 | 5/30 | 0/30 | 0/30 |
| 0.25 | 4 | 28/30 | 30/30 | — | — |
| 0.1 | 4 | 28/30 | 29/30 | — | — |

The results indicate that the minimum effective concentration of phthalaldehyde which is sporicidal at 20° C. in 24 hours is about 0.25% at both pH 8 and 6 and between 0.5% and 1.0% at pH 4.

EXAMPLE X

Solutions containing 0.3% phthalaldehyde buffered to pH 8 and pH 6 as in Example V were stored at 40° C. for 6 months to determine the effect of pH on the stability of the solutions under accelerated aging conditions. The results are shown in Table X.

TABLE X

| Storage time (months) | pH | % Phthal-aldehyde (±0.03%) |
|---|---|---|
| 0 | 8.00 | 0.28 |
| 2 | 7.87 | 0.28 |
| 6 | 7.76 | 0.32 |
| 0 | 6.00 | 0.26 |
| 2 | 5.99 | 0.26 |

TABLE X-continued

| Storage time (months) | pH | % Phthal-aldehyde (±0.03%) |
|---|---|---|
| 6 | 6.00 | 0.24 |

The results show that phthalaldehyde solutions have excellent storage stability at both alkaline and acidic pH.

EXAMPLE XI

Glass slides that were stained with 0.05 grams of human blood and dried for 5 minutes at 22° C. to 25° C. were immersed in two solutions containing 0.5% phthalaldehyde. The pH of both phthalaldehyde solutions was adjusted to pH 7.5. The compositions of the phthalaldehyde solutions only differed in the presence or absence of 0.2% nonionic surfactant. Observations of the blood removal properties for the phthalaldehyde solutions were made after 5 and 14 minutes contact time with the stained slides. The blood removal property of the solutions was graded on the basis of assigning a number from 1 to 7; where 1 signified no removal and 7 complete removal. The results were compared to the blood removal capabilities of a 2% glutaraldehyde solution (pH 7.5) with 0.2% nonionic surfactant. The results are shown in Table XI.

TABLE XI

| Test solutions | Cleaning ratings | |
|---|---|---|
| | 5 min. contact | 15 min. contact |
| 2% Glutaraldehyde/ 0.2% Surfactant | 1 | 3 |
| 0.3% Phthalaldehyde | 7 | 7 |
| 0.3% Phthalaldehyde/ 0.2% Surfactant | 7 | 7 |

The results show that phthalaldehyde compositions removed 100% of the blood in 5 minutes from the stained slides.

We claim:

1. An odorless high level disinfecting and sterilizing composition comprising an aqueous solution containing from 0.025 to 2.0 weight percent of phthalaldehyde, wherein said solution has disinfecting properties at a concentration of phthalaldehyde of from 0.025 to 2.0 weight percent and a pH of from 3 to 9, wherein said solution has sterilizing properties at a concentration of phthalaldehyde above about 0.5 weight percent and a pH of from 3 to 9, and wherein said solution has sterilizing properties at a concentration of phthalaldehyde of at least about 0.25 weight percent and a pH of from 6 to 8.

2. The composition of claim 1 in which the phthalaldehyde concentration is between 0.025% and 1.0%.

3. The composition of claim 1 in which the phthalaldehyde concentration is between 0.05% and 0.5%.

4. The composition of claim 1 having a pH in the range of between 3 and 9.

5. The composition of claim 1 which further comprises alkalinating or acidifying salts, surfactants, corrosion inhibitors, antioxidants, sequesterent, dye and fragrance.

* * * * *